US012802335B2

(12) United States Patent
Wahrenberg

(10) Patent No.: US 12,802,335 B2
(45) Date of Patent: Nov. 17, 2026

(54) MEDICAL IMAGE PROCESSING APPARATUS AND METHOD

(71) Applicant: CANON KABUSHIKI KAISHA, Tokyo (JP)

(72) Inventor: Magnus Fredrik Wahrenberg, Edinburgh (GB)

(73) Assignee: CANON KABUSHIKI KAISHA, Tokyo (JP)

( * ) Notice: Subject to any disclaimer, the term of this patent is extended or adjusted under 35 U.S.C. 154(b) by 293 days.

(21) Appl. No.: 18/613,374

(22) Filed: Mar. 22, 2024

(65) Prior Publication Data

US 2025/0299423 A1 Sep. 25, 2025

(51) Int. Cl.
*G06T 15/08* (2011.01)
*A61B 6/00* (2024.01)
(Continued)

(52) U.S. Cl.
CPC ............ *G06T 15/08* (2013.01); *G06T 7/0012* (2013.01); *G06T 7/11* (2017.01); *G06T 7/60* (2013.01);
(Continued)

(58) Field of Classification Search
CPC ......... G06T 15/08; G06T 7/0012; G06T 7/11; G06T 7/60; G06T 2207/30101;
(Continued)

(56) References Cited

U.S. PATENT DOCUMENTS 5,915,036 A 6/1999 Grunkin et al.
10,417,759 B2 9/2019 Reynolds
(Continued)

FOREIGN PATENT DOCUMENTS

CN 203837658 U 9/2014
CN 109859233 A 6/2019
(Continued)

OTHER PUBLICATIONS

S. Piccand, R. Noumeir and E. Paquette, "Region of Interest and Multiresolution for Volume Rendering," in IEEE Transactions on Information Technology in Biomedicine, vol. 12, No. 5, pp. 561-568, Sep. 2008, doi: 10.1109/TITB.2007.907986. (Year: 2008).*
(Continued)

*Primary Examiner* — Xiao M Wu
*Assistant Examiner* — Latrell Anthony Creary
(74) *Attorney, Agent, or Firm* — Oblon, McClelland, Maier & Neustadt, L.L.P.

(57) ABSTRACT

A medical image processing apparatus includes processing circuitry configured to receive a slab comprising a plurality of samples determined by a camera model, determine whether one or more first samples of the plurality of samples are part of an anatomical region of interest, and project the slab along a view direction onto an image plane to form an image. In response to a determination that the one or more first samples are part of the anatomical region of interest, the processing circuitry is configured to project the one or more first samples using a first projection mode and project one or more second samples of the plurality of samples that are not part of the anatomical region of interest using a second projection mode.

19 Claims, 9 Drawing Sheets

(51) Int. Cl.
*G06T 7/00* (2017.01)
*G06T 7/11* (2017.01)
*G06T 7/60* (2017.01)

(52) U.S. Cl.
CPC ... *A61B 6/5247* (2013.01); *G06T 2207/30101* (2013.01); *G06T 2210/41* (2013.01)

(58) Field of Classification Search
CPC ....... G06T 2210/41; G06T 2207/30061; G06T 7/64; G06T 2207/20084; A61B 6/5247
See application file for complete search history.

(56) References Cited

U.S. PATENT DOCUMENTS

| | | | |
|---|---|---|---|
| 2007/0086672 A1 | 4/2007 | Zeng et al. | |
| 2007/0274584 A1 | 11/2007 | Leow et al. | |
| 2010/0280382 A1 | 11/2010 | Margaliot et al. | |
| 2013/0249913 A1 | 9/2013 | Smout et al. | |
| 2014/0035916 A1 | 2/2014 | Murphy et al. | |
| 2016/0071264 A1* | 3/2016 | Agam | G06T 7/0012 382/128 |
| 2017/0262978 A1* | 9/2017 | Reynolds | G06T 3/067 |
| 2018/0329609 A1 | 11/2018 | De Swarte et al. | |
| 2020/0074712 A1 | 3/2020 | Wu et al. | |
| 2025/0138709 A1* | 5/2025 | Boucneau | G06F 3/04847 |
| 2025/0285284 A1* | 9/2025 | Yerebakan | G06T 7/11 |
| 2025/0299824 A1* | 9/2025 | Benech | G06T 7/0012 |

FOREIGN PATENT DOCUMENTS

| | | |
|---|---|---|
| CN | 111325745 A | 6/2020 |
| CN | 111462071 A | 7/2020 |
| CN | 111627005 A | 9/2020 |
| CN | 112201239 A | 1/2021 |
| CN | 112241955 A | 1/2021 |
| CN | 112489005 A | 3/2021 |
| CN | 114494160 A | 5/2022 |
| CN | 115311491 A | 11/2022 |
| KR | 10-2018-0061888 A | 6/2018 |
| WO | WO 2020/093987 A1 | 5/2020 |
| WO | WO 2021/071288 A1 | 4/2021 |
| WO | WO 2022/139246 A1 | 6/2022 |

OTHER PUBLICATIONS

Bob D. de Vos, Jelmer M. Wolterink, Pim A. de Jong, et al. "2D image classification for 3D anatomy localization: employing deep convolutional neural networks", Proc. SPIE 9784, Medical Imaging 2016: Image Processing, 97841Y (Mar. 21, 2016); https://doi.org/10.1117/12.2216971 (Year: 2016).*

Hauser et al., "Two-Level vol. Rendering", IEEE Transactions on Visualization and Computer Graphics, vol. 7, No. 3, Jul.-Sep. 2001, pp. 242-252 (Total 12 pages).

Frangi et al., "Multiscale Vessel Enhancement Filtering", In Medical Image Computing and Computer-Assisted Intervention, Lecture Notes in Computer Science, vol. 1496, Feb. 2000, 9 pages.

Wasserthal et al., "Total Segmentator: Robust Segmentation of 104 Anatomic Structures in CT Images", Radiology: Artificial Intelligence, vol. 5, No. 5, 2023, 9 pages.

Jönsson et al., "A Survey of Volumetric Illumination Techniques for Interactive Volume Rendering", Computer Graphics forum, vol. 33, No. 1, 2014, 27 pages.

Murphy, "Maximum Intensity Projection", Radiology Reference Article, retrieved from https://radiopaedia.org/articles/maximum-intensity-projection, Mar. 23, 2023, 6 pages.

* cited by examiner

MEDICAL IMAGE PROCESSING APPARATUS AND METHOD

FIELD

The present invention relates to a medical image processing apparatus and a medical image processing method.

BACKGROUND

Volume rendering is a process of calculating two-dimensional (2D) images of three-dimensional (3D) objects. An application of volume rendering is in the field of rendering of medical volume data resulting, for example, from the scanning of the human body using computed tomography (CT) and other X-ray scanners, nuclear magnetic resonance scanners, ultrasound scanners or other medical scanners.

Volume data comprises a plurality of voxels arranged in a 3D grid. Each voxel has a voxel value associated with it. The voxel values represent measurements of a physical parameter. For example, in the case of CT scans, the voxel values represent the opacity of those voxels to X-rays, i.e. their X-ray stopping power. X-ray stopping power is measured in Hounsfield units (HUs) which is closely correlated with density (mass per unit volume).

The voxels of volume data acquired by a medical scanner are in most cases acquired on a Cartesian grid, i.e. the data points are aligned along three orthogonal axes, which define a volume space.

A 2D image comprises a plurality of image pixels arranged in a 2D grid. A view space can be defined by three orthogonal axes X, Y and Z, which have a common origin at one corner of the image. The X- and Y-axes span an image plane and are aligned with the 2D grid of pixels. The Z-axis is perpendicular to the image plane and is parallel to with a view direction.

Images may be generated from the volume data using a conventional slab Multi-Planar Reformatting (MPR) method. In this method, MPR data are generated by taking a coordinate in view space, transforming the coordinate into volume space, and sampling the volume data, e.g. using an interpolation method, such as a trilinear interpolation method, to generate a MPR data value for the discrete view space coordinate. The MPR data value is also be referred to as a MPR sample. A MPR slice may be formed by carrying this out for a plurality of coordinates in an image plane. If this is repeated in the view direction, which is perpendicular to the image plane, then multiple MPR slices can be determined and these slices can be projected to form a MPR slab. The MPR slab can thus comprise a series of MPR slices, which are aligned parallel to the image plane and disposed at different positions along the view direction.

A 2D image can be formed by projecting (collapsing) the MPR slab along the view direction onto the image plane. This can be done according to a projection algorithm. Maximum Intensity Projection (MIP), Minimum Intensity Projection (MinIP) and Average Intensity Projection (AveIP) are examples of projection algorithms that may be used for projecting the MPR slab.

For example, the MIP algorithm is based on determining for each image pixel the maximum voxel value seen in the MPR slab along the Z-axis for the XY-coordinate corresponding to that image pixel. MIP is a type of ray casting. For each pixel in the image, an imaginary ray is cast through the volume data parallel to the view direction. The image data for each pixel is then taken to be the maximum voxel value encountered by the ray as it traverses the MPR slab.

The MinIP algorithm uses the minimum voxel value encountered by rays traversing the MPR slab for the image data instead of the maximum. In AveIP, the voxel data values sampled from the portion of the ray traversing the slab are averaged to produce their collective value.

When using these projection algorithms, it may be difficult to visualise thin and/or small spatial features that may be part of or define an anatomical region of interest. For example, when using these projection algorithms, it may be difficult to visualise a thin fracture in a bone in the projected image. This in turn may make it difficult to determine a size and/or extent of the fracture.

DESCRIPTION

Embodiments are now described by way of non-limiting example with reference to the accompanying drawings in which.

Figure 2A:
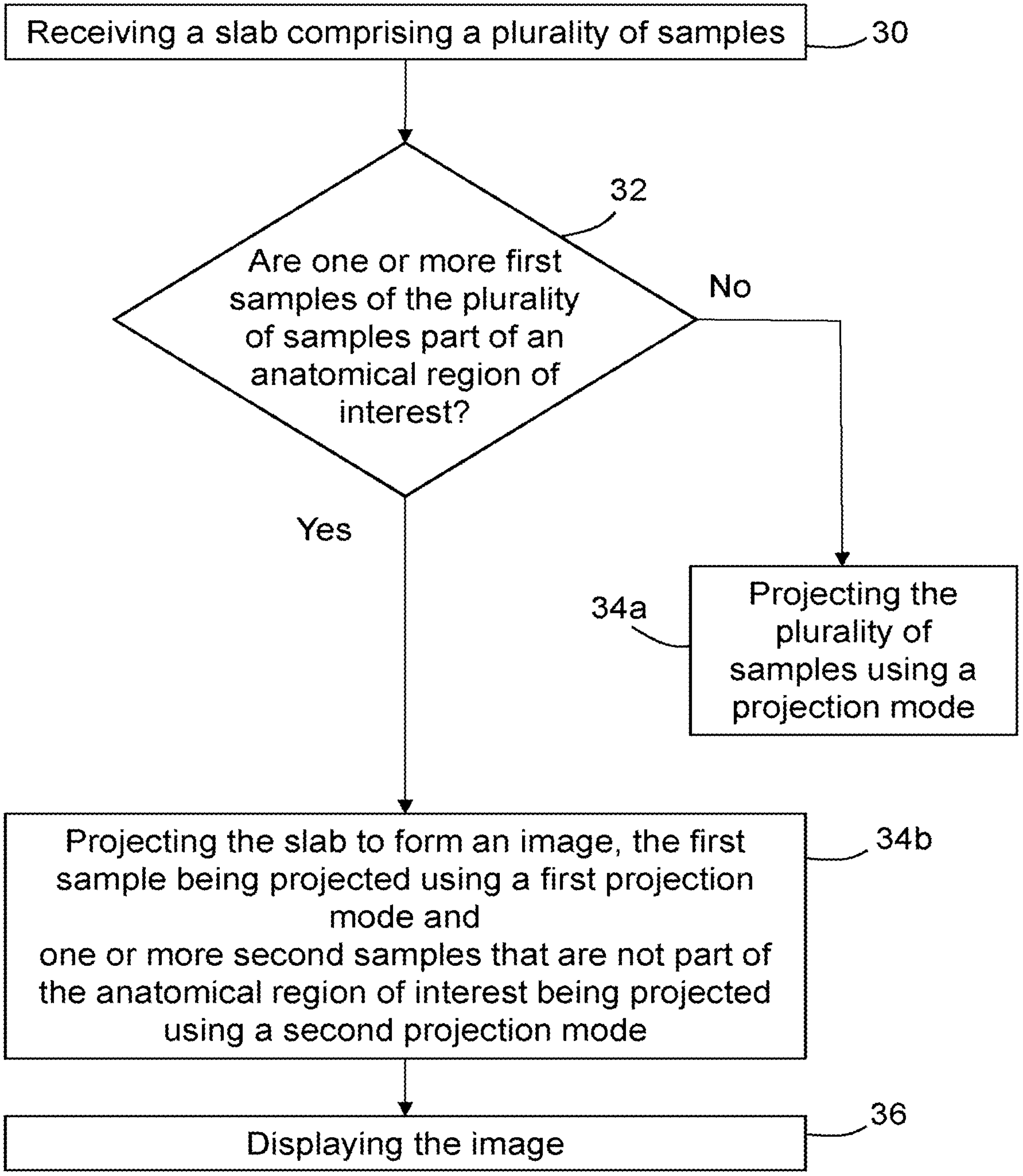
FIG. 2A is a flow chart illustrating in overview a process of an embodiment.
Figure 2B:
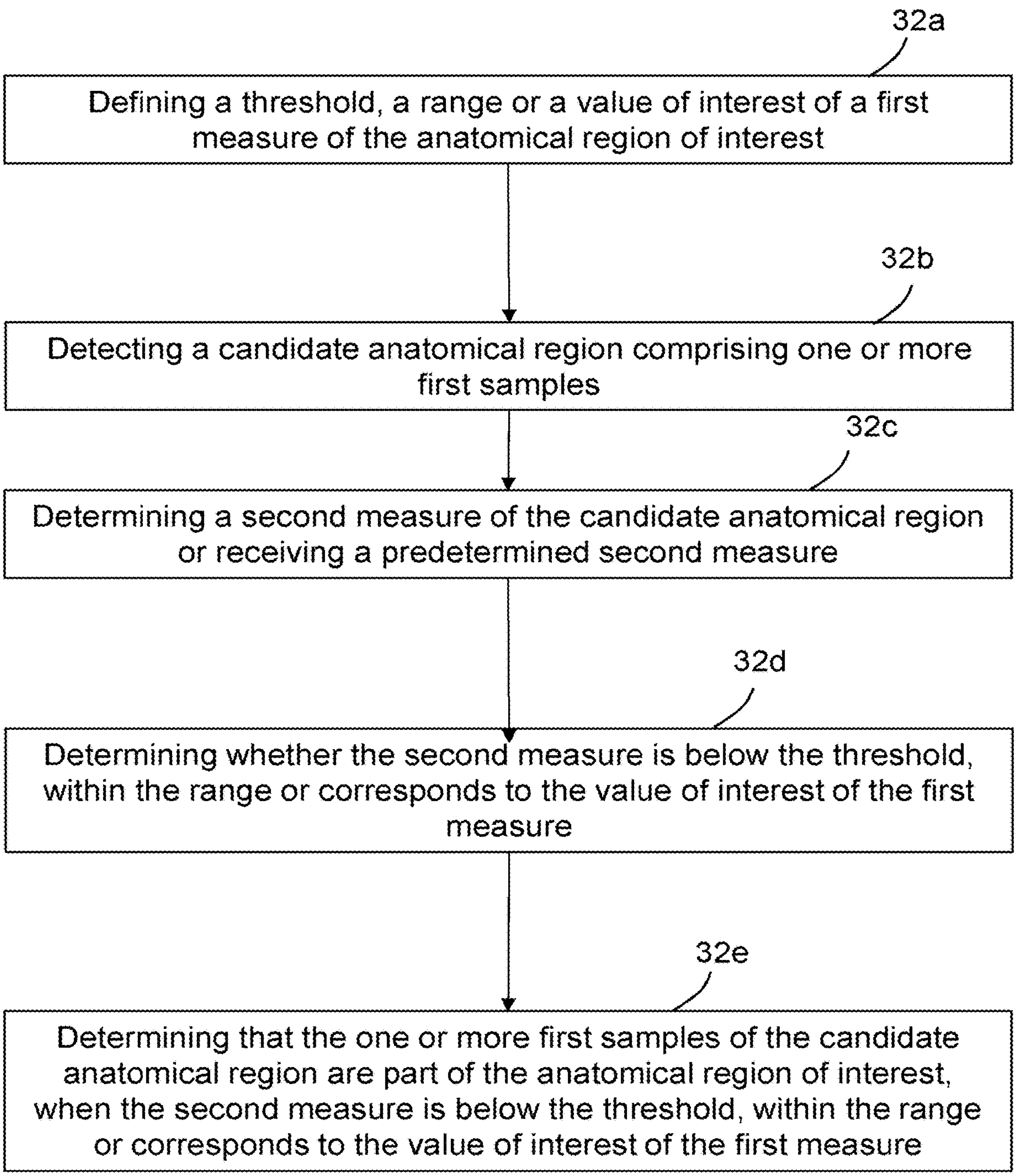
FIG. 2B illustrates further steps that may be part of the process illustrated in FIG. 2A.
Figure 3:
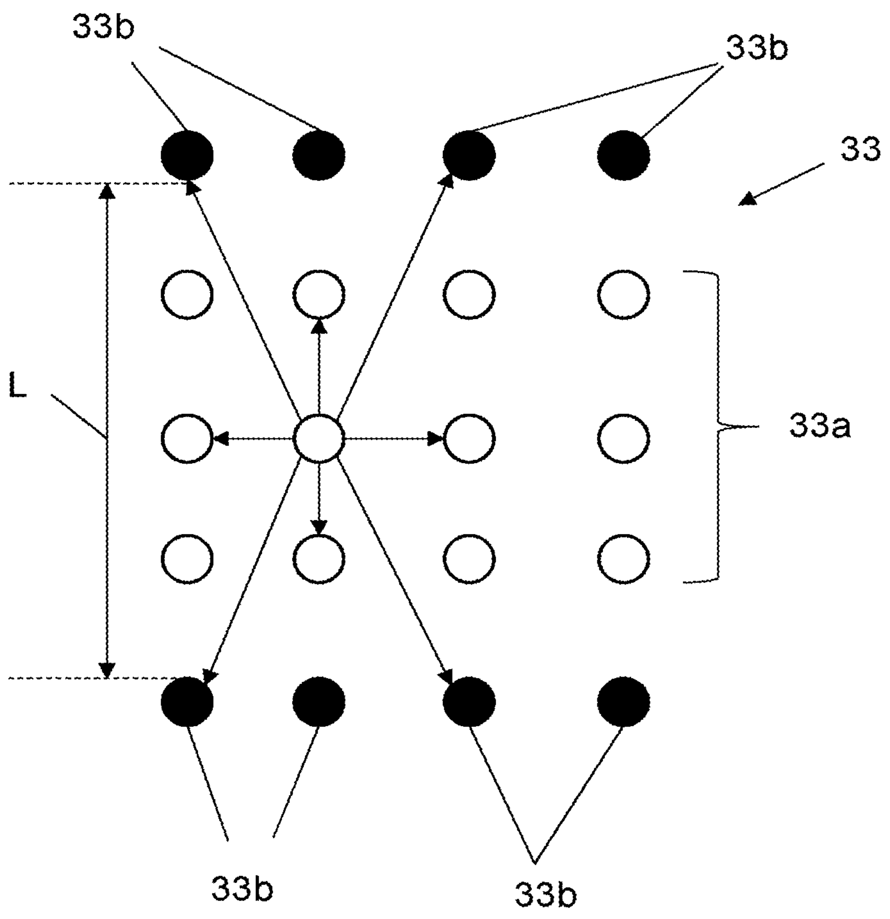
Figure 4A:
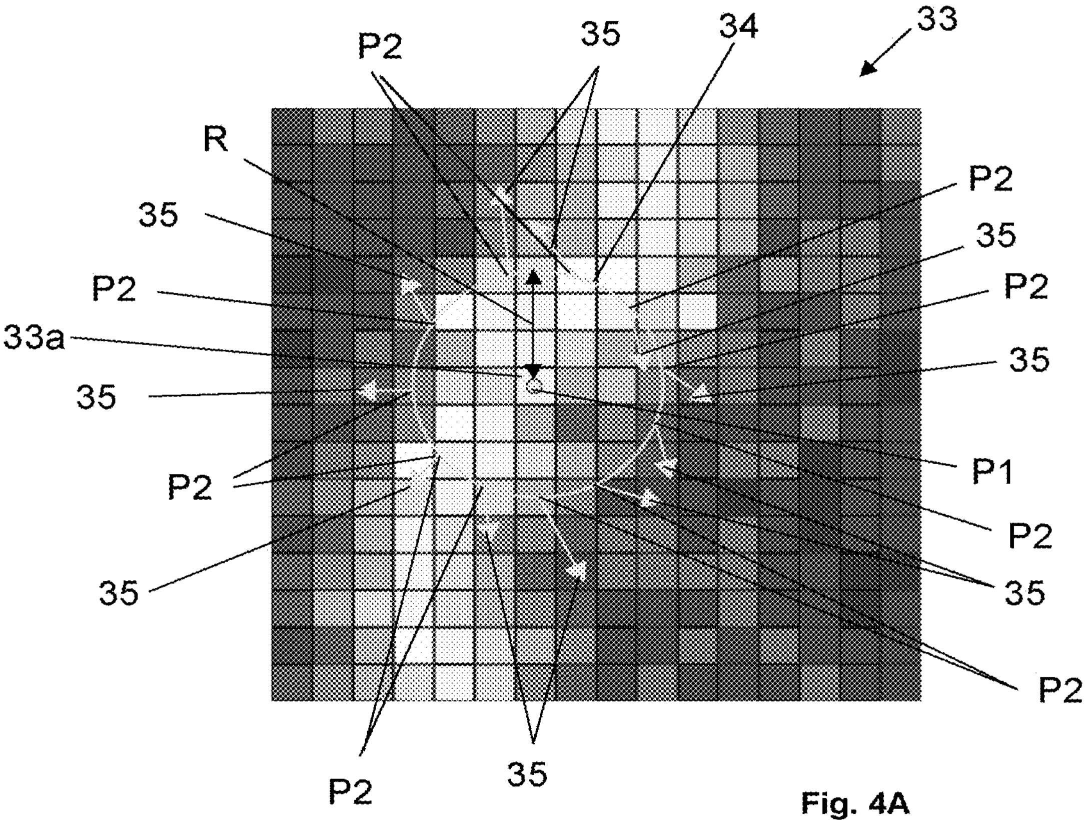
Figure 4B:
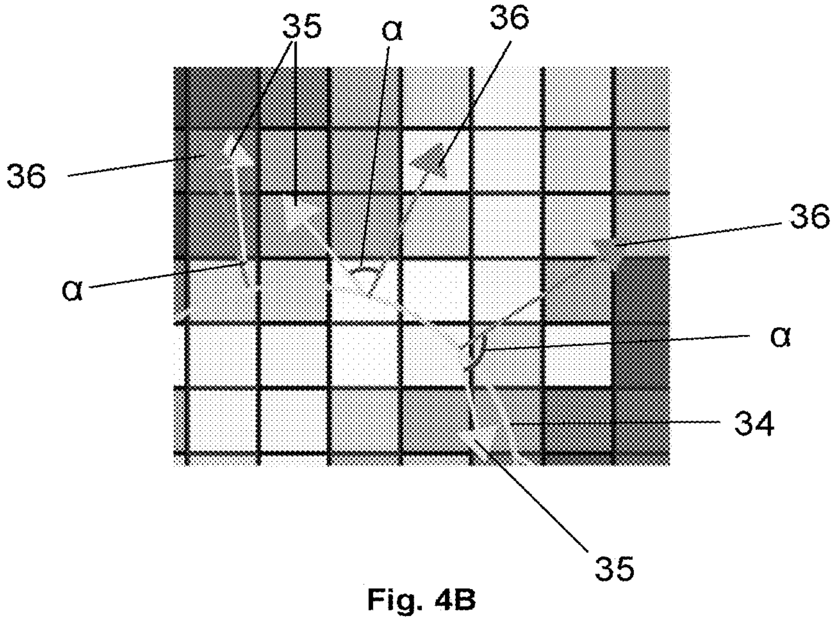
Figure 5A:
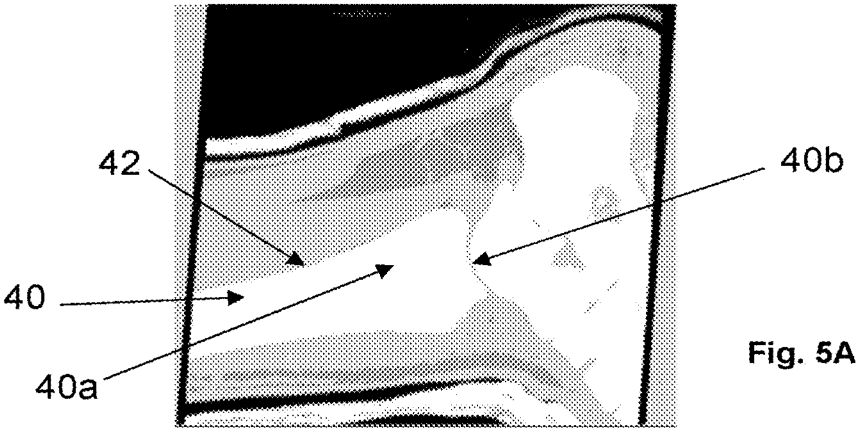
Figure 5B:
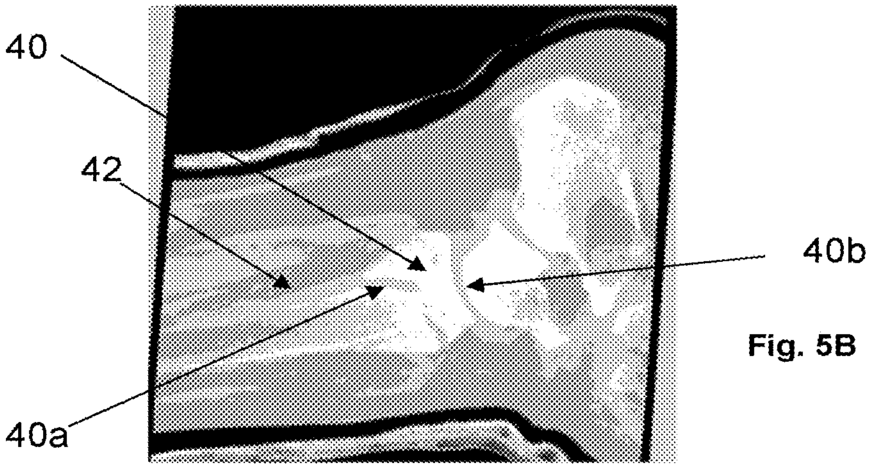
Figure 5C:
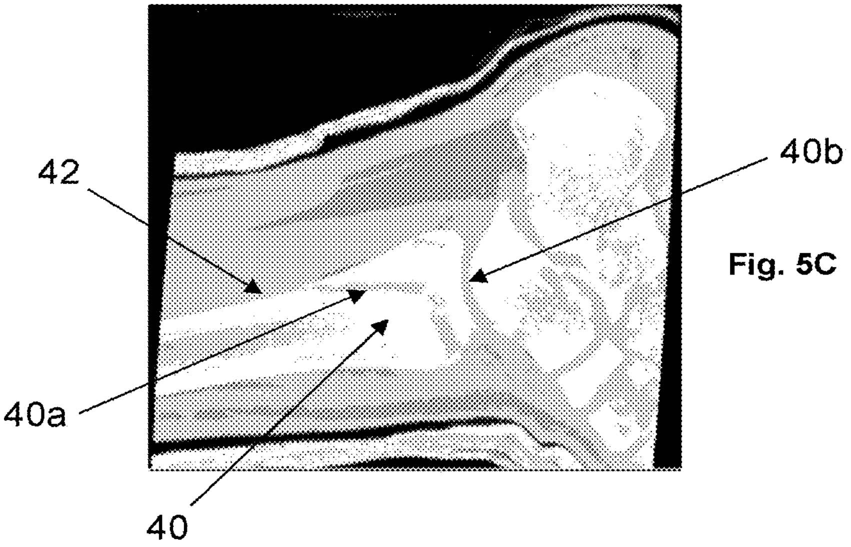
Figure 6A:
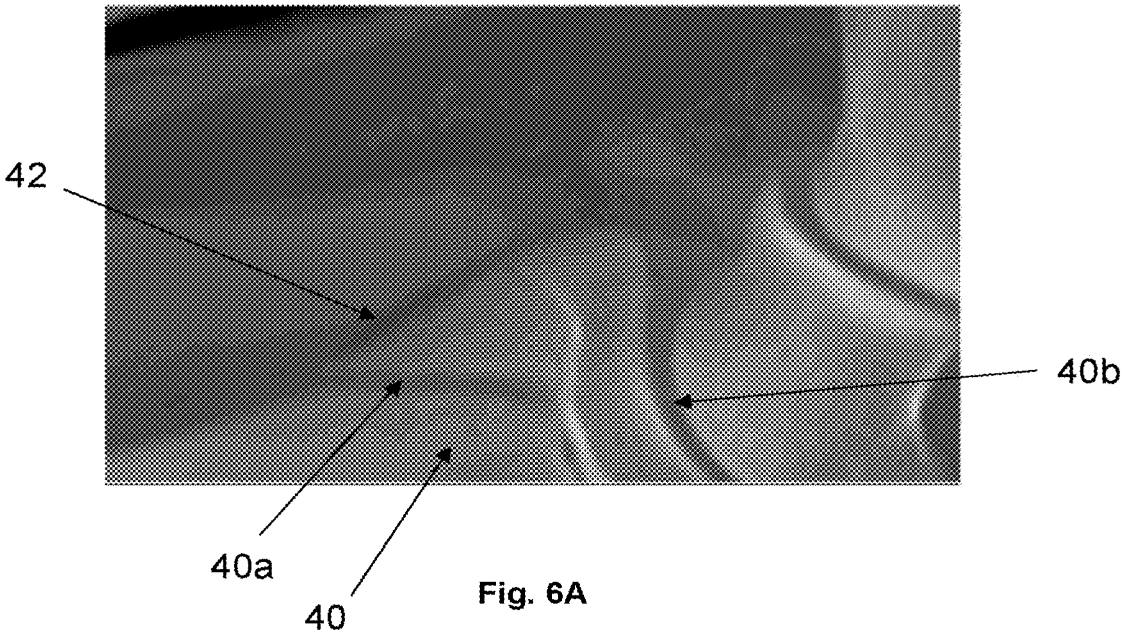
Figure 6B:
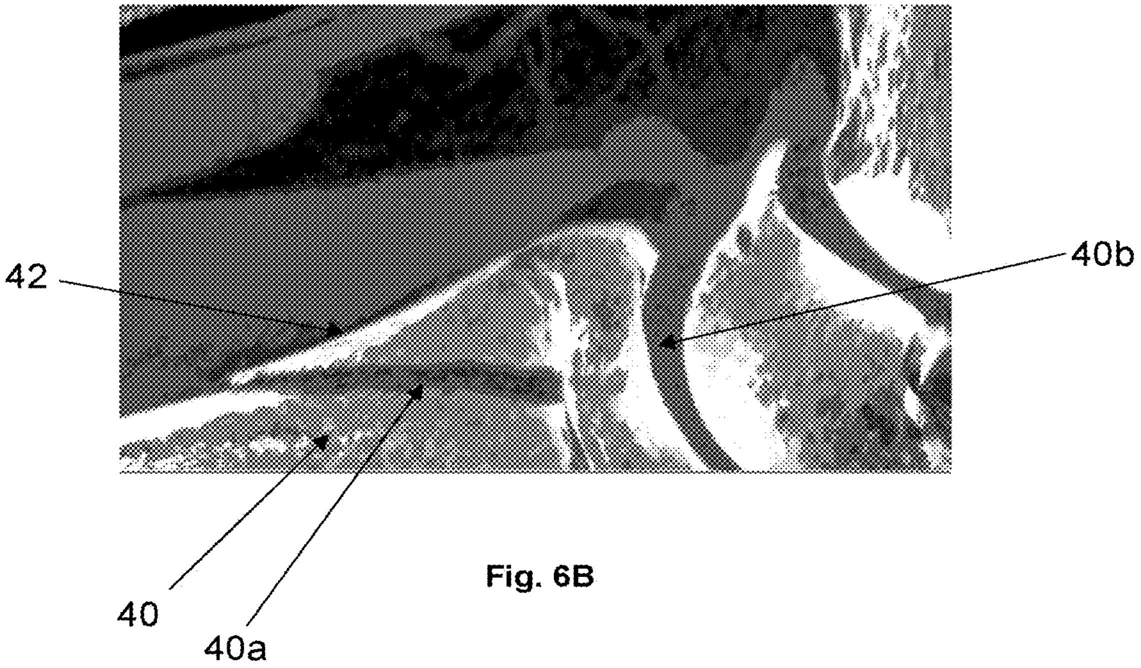
Figure 7:
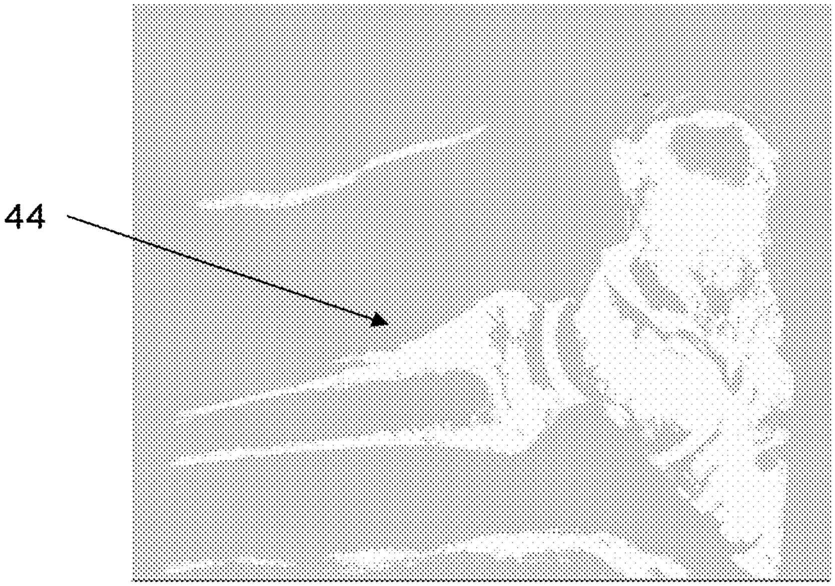
Figure 8:
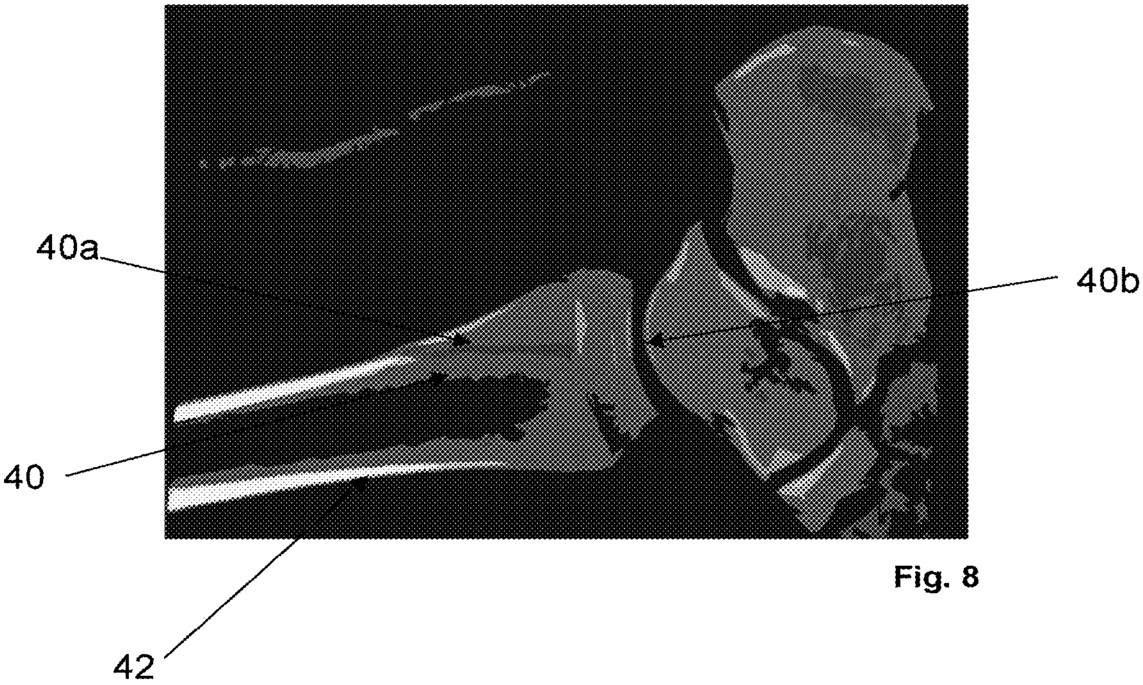
Figure 9:
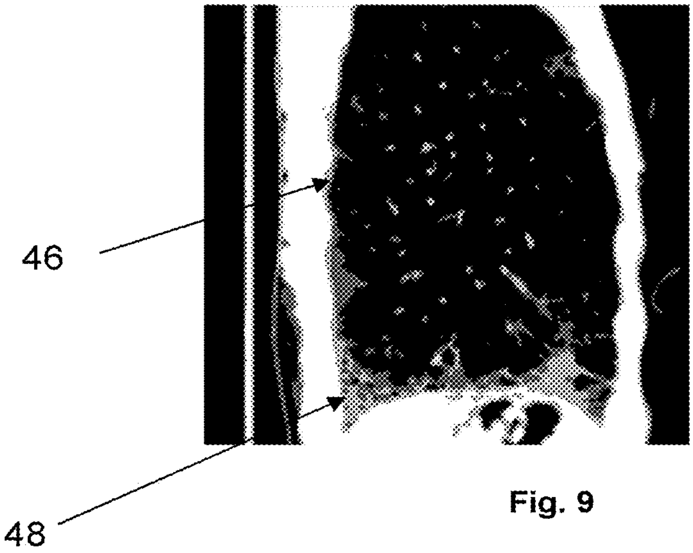
Figure 10:
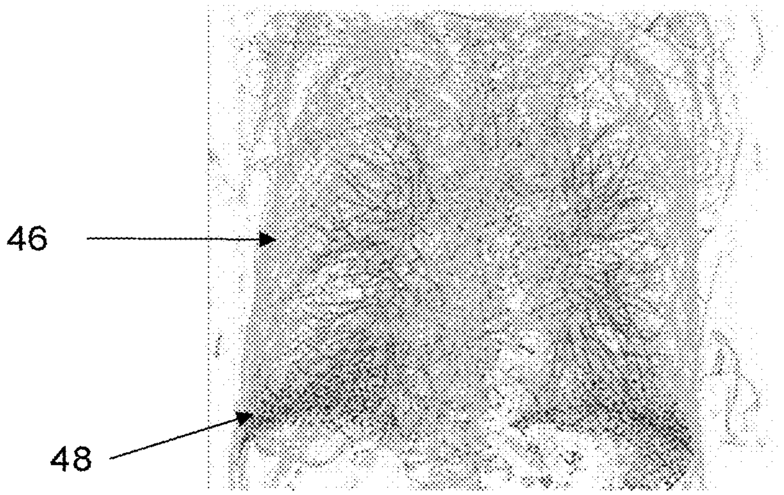

FIG. 3 schematically illustrates an exemplary candidate region, which may be detected in one of the further steps illustrated in FIG. 2B;

FIG. 4A illustrates a schematic representation of a sphere generated as part of a sphericity filtering method, which may be part of one of the further steps illustrated in FIG. 2B;

FIG. 4B illustrates a schematic representation of a part of the sphere of FIG. 4A, including a plurality of expected gradient vectors;

FIG. 5A illustrates a two-dimensional image of an anatomical region of interest that has been generated by projecting a MPR slab using a Maximum Intensity Projection mode;

FIG. 5B illustrates a two-dimensional image of the anatomical region of interest that has been generated by projecting a MPR slab using a Minimum Intensity Projection mode;

FIG. 5C illustrates a two-dimensional image of the anatomical region of interest that has been generated using the process of FIGS. 2A and 2B;

FIG. 6A illustrates a two-dimensional image of the anatomical region of interest that has been generated by projecting a MPR slab using an Average Intensity Projection mode;

FIG. 6B illustrates a two-dimensional image of the anatomical region of interest that has been generated using the process of FIGS. 2A and 2B;

FIG. 7 illustrates a two-dimensional image of a mask that is defined by pixels associated with the anatomical region of interest;

FIG. 8 illustrates another two-dimensional image of the anatomical region of interest that has been generated using the process of FIGS. 2A and 2B;

FIG. 9 illustrates a two-dimensional image of another anatomical region of interest that has generated by projecting a MPR slab using the Maximum Intensity Projection mode; and FIG. 10 illustrates a two-dimensional image of the anatomical region of interest of FIG. 9, the image having been generated using the process of FIGS. 2A and 2B.

Certain embodiments provide a medical image processing apparatus comprising processing circuitry configured to receive a slab comprising a plurality of samples determined by a camera model, determine whether one or more first samples of the plurality of samples are part of an anatomical region of interest, project the slab along a view direction onto an image plane to form an image, wherein in response to a determination that the one or more first samples are part of the anatomical region of interest, the processing circuitry is configured to project the one or more first samples using a first projection mode and project one or more second samples of the plurality of samples that are not part of the anatomical region of interest using a second projection mode.

Certain embodiments provide a medical image processing method comprising receiving a slab comprising a plurality of samples determined by a camera model, determining whether one or more first samples of the plurality of samples are part of an anatomical region of interest, projecting the slab along a view direction onto an image plane to form an image, wherein in response to a determination that the one or more first samples are part of the anatomical region of interest, the method comprises projecting the one or more first samples using a first projection mode and projecting one or more second samples of the plurality of samples that are not part of the anatomical region of interest using a second projection mode.

Figure 1:
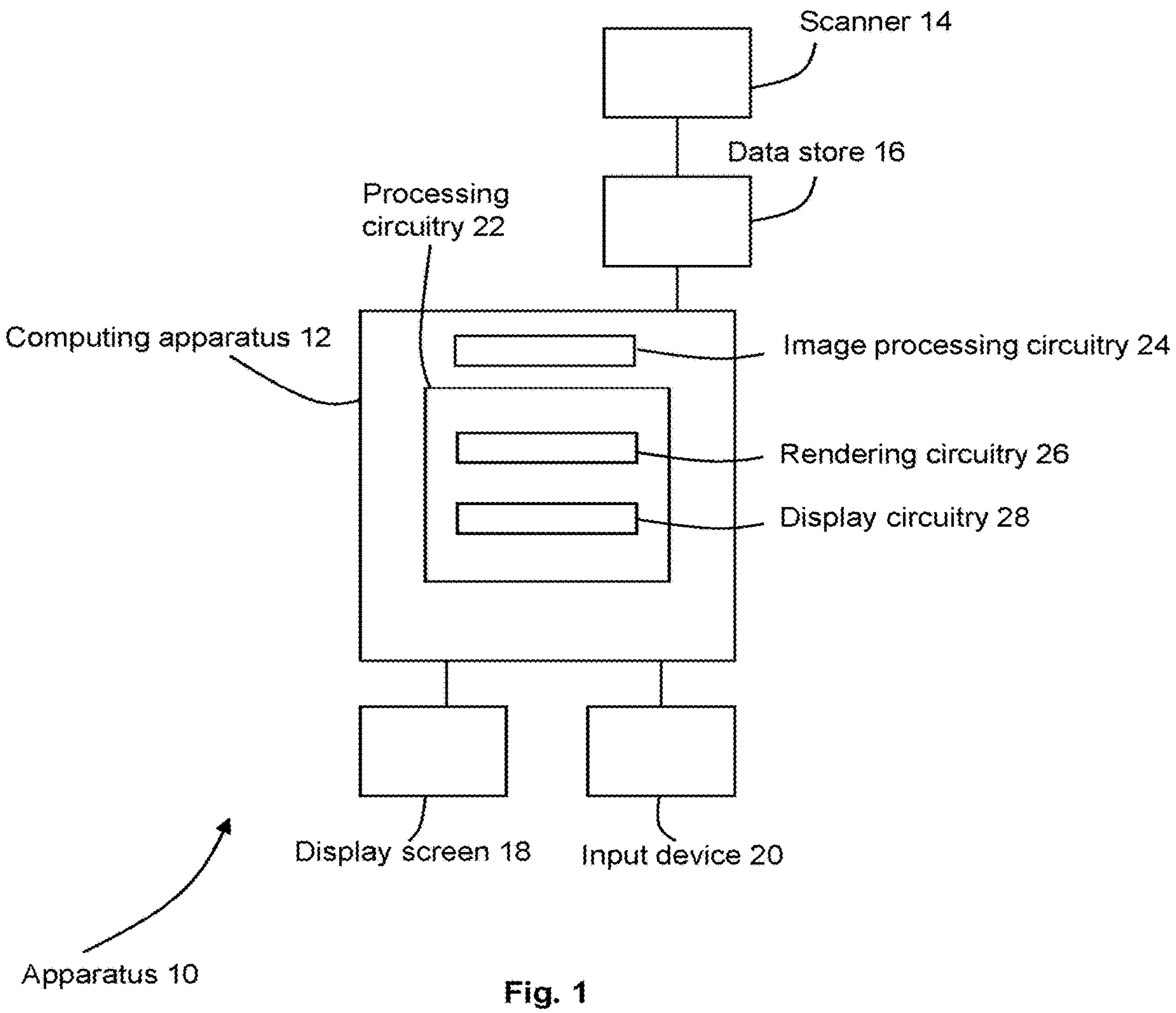
FIG. 1 is a schematic illustration of a medical image processing apparatus according to an embodiment.

A medical image processing apparatus 10 according to an embodiment is schematically illustrated in FIG. 1. The medical image processing apparatus 10 comprises a computing apparatus 12, which may be provided in the form of a personal computer or workstation. In this embodiment, the computing apparatus 12 is connected to a scanner 14, e.g. via a data store 16. However, it will be appreciated that in other embodiments, the medical image processing apparatus may not be connected or coupled to any scanner.

The medical image processing apparatus 10 further comprises one or more display screens 18 and an input device or devices 20, such as a computer keyboard, mouse or trackball.

In the present embodiment, the scanner 14 is a computed tomography (CT) scanner. However, it will be appreciated that in other embodiments the scanner may comprise another medical scanner, such as a nuclear magnetic resonance scanner, an ultrasound scanner or another medical scanner. The scanner 14 is configured to generate image data that is representative of an anatomical region of a patient or other subject.

In the present embodiment, image data sets obtained by the scanner 14 are stored in the data store 16 and subsequently provided to the computing apparatus 12. In an alternative embodiment, image data sets may be supplied from a remote data store (not shown). The data store 16 or remote data store may comprise any suitable form of memory storage.

The computing apparatus 12 comprises a processing circuitry 22 for processing of data. The processing circuitry comprises a central processing unit (CPU) and Graphical Processing Unit (GPU). The processing circuitry 22 provides a processing resource for automatically or semi-automatically processing medical image data sets. In other embodiments, the data to be processed may comprise any image data, which may not be medical image data.

In the present embodiment, the computing apparatus 12 comprises image processing circuitry 24 for generating a slab comprising a plurality of samples determined by a camera model. The slab may be generated according to the Multi-Planar Reformatting (MPR) method mentioned above. However, it will be appreciated that the slab may be generated by using another reformatting method. For example, the slab may be generated according to a Curved Planar Reformatting (CPR) method, the reformatting method described in US 2017/0262978 A1 or any other reformatting method. The image processing circuitry 24 can be configured to transmit the slabs to the processing circuitry 22 for further processing. It will be appreciated that in other embodiments, the processing circuitry may receive the slab from the data store.

The camera model defines the view direction mentioned above. For example, using a simple camera model, a ray starts at a centre of projection of the camera and passes through the image pixel on the image plane between the camera the 3D volume. It will be appreciated that any kind of camera model may be used, such as a fish eye camera model, a mixed view cameral model, a Curved Planar Reformation (CPR) based camera model of another camera model. The CPR based camera model may comprise a projected CPR based camera model, stretched CPR based camera model, straightened CPR based camera model or the like.

In the present embodiment, the processing circuitry 22 comprises rendering circuitry 26 configured to project the slab into a two-dimensional (2D) image. For example, the rendering circuitry may be configured to use one or more projection algorithm, such as the MIP algorithm, the MinIP algorithm, the AveIP algorithm, as described above, and/or another projection algorithm, to project the slab into the 2D image.

In the present embodiment, the processing circuitry 22 comprises display circuitry 28 configured to display the 2D image to a user on the display screen 18.

In the present embodiment, the circuitries 22, 24, 26, 28 are each implemented in the CPU and/or GPU by means of a computer program having computer-readable instructions that are executable to perform one or more operations of the medical image processing apparatus 10 and/or a medical image processing method of an embodiment described herein. In other embodiments, the circuitries may be implemented as one or more ASICs (application specific integrated circuits) or FPGAs (field programmable gate arrays).

The computing apparatus 12 also includes a hard drive and other components of a PC including RAM, ROM, a data bus, an operating system including various device drivers, and hardware devices including a graphics card. Such components are not shown in FIG. 1 for the sake of clarity.

FIG. 2A is a flow chart illustrating in overview a process of an embodiment.

At a first stage 30, the processing circuitry 22 is configured to receive the slab comprising the plurality of samples determined by the camera model.

At stage 32, the processing circuitry 22 is configured to determine whether one or more first samples of the plurality of samples are part of an anatomical region of interest. The anatomical region of interest may also be referred to as an anatomical structure of interest. An exemplary anatomical region of interest may include, but not limited to, a gap or space in a tissue and/or between different tissues, a tubular structure, e.g. a substantially tubular structure, a spherical structure, e.g. substantially spherical structure, or another structure. For example, a gap or space in a tissue may comprise a bone fracture or a gap or space between at least two different bones. A tubular structure may comprise a vessel or part thereof. A spherical structure may comprise an abnormality or the like.

At stages 34*a*, 34*b*, the processing circuitry 22 is configured to project the slab along the view direction onto the image plane to form an image. The image is also referred to as a two-dimensional (2D) image.

In response to a determination that the first samples are not part of the anatomical region of interest, at stage 34*a*, the processing circuitry 22 may be configured to project the plurality of samples using a projection algorithm, such as the MIP algorithm, the MinIP algorithm, the AveIP algorithm or another projection algorithm.

In response to a determination that the first samples are part of the anatomical region of interest, at stage 34*b*, the processing circuitry 22 is configured to project the first samples using a first projection mode. The processing circuitry 22 is further configured to project one or more second samples of the plurality of samples that are not part of the region of interest using a second projection mode.

In some embodiments, the first and second projection modes are the same. In other embodiments, the first and second projections modes are different. The first projection mode includes at least one of the MIP algorithm, the MinIP algorithm, the AveIP algorithm or another projection algorithm. The second projection mode includes at least one of the MIP algorithm, the MinIP algorithm, the AveIP algorithm or another projection algorithm.

In embodiments where the first and second projection modes are different, at least one of the first and second projection modes comprises the MinIP algorithm and at least one other of the first and second projection modes comprises the MIP algorithm.

In embodiments where the first and second projections modes are the same, the processing circuitry 22 is configured to project the first samples separately from the second samples. For example, the processing 22 circuitry may be configured to project the first samples using the AveIP algorithm. This includes only averaging voxel data associated with the first samples. The processing circuitry 22 may be configured be configured to project the second sample using the AveIP algorithm. This includes only averaging voxel data associated with the second samples.

At stage 36, the processing circuitry 22 is configured to display the image. For example, the display circuitry 28 may be configured to display the image on the display screen 18. However, it will be appreciated that in some embodiments, the image may not be displayed. For example, in such other embodiments, the image may be further processed, stored and/or transmitted to another computing apparatus.

FIG. 2B illustrates further steps that may be part of the process illustrated in FIG. 2A.

At stage 32*a*, the processing circuitry 22 is configured to define a threshold, a range or a value of interest of a first measure of the anatomical region of interest, e.g. in response to a user instruction.

In some embodiments, the value of interest of the first measure may comprise a maximum value of the first measure. However, it will be appreciated that in other embodiments, the value of interest may comprise a different value, such as an average value of the first measure or another value of the first measure.

In examples where the anatomical region of interest comprises the gap or space, the first measure may comprise a dimension or size of the gap or space. The threshold, range or value of interest determines which first samples of which gap or space sizes or dimensions are to be projected using the first projection mode.

In examples where the anatomical region of interest comprises a tubular structure, the first measure may comprise a vesselness, vessel branching or another measure.

In examples where the anatomical region of interest comprises a spherical structure, the first measure may comprise a textural measure, such as a sphericity and/or variance, or another measure. The first measure can also be referred to as a metric. The term "sphericity" may be considered as a measure indicative on how spherical the anatomical region of interest is.

The threshold, range, or values of interest of the first measure can be defined based on a selected window width and/or window level to be applied to the 2D image. For example, the window width may comprise a selected range of voxel values of the slab. The window level may be understood as a midpoint of the range of voxel values, e.g. the window width. A lower bound of the window width corresponds to the window level minus a half of the window width and an upper bound of the window width corresponds to the window level plus a half of the window. For example, the threshold or range may be selected to be between 25% and 50% of the selected range of voxel values. The window level may also be referred to as W/L.

The selected range of voxel values can be associated with a type of tissue of the anatomical region of interest. The type of tissue may include soft tissue, such as muscle, tendons, ligaments, fat, fibrous tissues, blood vessels or other soft tissue, or hard tissue, such as bone or another hard tissue. In examples where the region of interest includes hard tissue, such as bone, the selected range of voxel values comprises voxel values for bone. It will be appreciated that the present disclosure is not limited to an anatomical region of interest comprising hard tissue, such as bone.

At stage 32*b*, the processing circuitry 22 is configured to detect a candidate anatomical region. The candidate anatomical region may be understood as a detected anatomical region or structure that will be evaluated to check whether it is the anatomical region of interest.

FIG. 3 schematically shows an exemplary candidate anatomical region 33. The candidate anatomical region 33 comprises the first samples mentioned above, which are indicated by reference numeral 33*a* in FIG. 3. In the embodiment shown in FIG. 3, the candidate anatomical region 33 comprises twelve first samples 33*a*. However, it will be appreciated that in other embodiments, the candidate anatomical region may comprise more or less than twelve first samples. The processing circuitry 22 can be configured to cast a plurality of lines from at least one first sample 33*a* in a plurality of directions. The plurality of lines are indicated by the arrows in FIG. 3. The plurality of directions may comprise a plurality of random directions, a random uniform distribution of directions on a sphere, a non-random uniform distribution of directions on a sphere, e.g. a Fibonacci sphere, which is schematically indicated in FIG. 3, or another distribution of directions. The plurality of directions are different from the view direction defined by the camera model. In FIG. 3, the plurality of lines are shown as being cast from a single first sample 33*a*. However, it will be appreciated that the processing circuitry 22 can be configured to cast the plurality of lines in the plurality of directions from each first sample 33*a*. The first sample 33*a* is associated with a first type of tissue or a first fluid. The processing circuitry 22 can be configured to detect one or more other first samples 33*a* that are associated with the same first type of tissue or fluid. The processing circuitry 22 can further be configured to detect one or more second samples 33*b* that are associated with a second type of tissue or a second fluid that is adjacent to the first type of tissue or first fluid. The second type of tissue or second fluid is different from the first type of tissue or first fluid. The detection of the second samples

33*b* can be indicative of the candidate anatomical region 33. In examples where the candidate anatomical region (and the anatomical region of interest) comprises the gap or space, the gap or space may be filled with the first tissue or first fluid. For example, a fracture in a bone can be filled with a fluid. As such, the first fluid comprises the fluid in the facture and the second tissue comprises bone. The/each first sample 33*a* of the candidate anatomical region 33 may also be referred to as potential gap candidate.

In examples where the anatomical region of interest comprises the tubular structure, the processing circuitry 22 is configured to use a vesselness filtering method to detect the candidate anatomical region. An exemplary vesselness filtering method that may be used by the processing circuitry 22 is described in A. F. Frangi et al. (1998) "Multiscale vessel enhancement filtering". In Medical Image Computing and Computer-Assisted Intervention—MICCAI '98, Lecture Notes in Computer Science, vol. 1496-Springer Verlag, Berlin, Germany, pp. 130-137. This vesselness filtering method may allow for a vesselness measure or vessel branching to be obtained on the basis of all eigenvalues of a local Hessian matrix. For example, this vesselness filtering method uses Gaussian derivative kernels to form a scale specific Hessian matrix. The processing circuitry 22 can be configured to evaluate the eigenvalues of the Hessian matrix to determine the vesselness or vessel branching. The obtained vesselness or vessel branching may be indicative of the candidate anatomical region.

In examples where the anatomical region of interest comprises the spherical structure, the detection of the candidate anatomical region may be based on a sphericity measurement or the like. For example, the processing circuitry 22 can be configured to use or perform a sphericity filtering method to detect the candidate anatomical region 33.

The sphericity filtering method can comprise generating for each first sample of the candidate anatomical region 33 a uniform set of points P2 on a sphere 34 centred on a first sample 33*a*. FIG. 4A shows a schematic representation of the generated sphere 34, which is indicated by a circle. A centre of the sphere 34 is indicated by reference numeral P1 in FIG. 4A. Only one first sample 33*a* is indicated in FIG. 4A for sake of clarity. However, it will be appreciated that the candidate anatomical region 33 may comprise more than one first sample and/or more than one generated sphere. For example, the processing circuitry 22 may be configured to generate a plurality of overlapping spheres. The plurality of overlapping spheres may define a tightly packed arrangement or grid of spheres.

In the embodiment shown in FIG. 4A, the set of points comprises eleven points P2. However, it will be appreciated that in other embodiments, the set of points may comprise more or less than eleven points. The sphere 34 has a fixed radius R. The radius R may depend on an expected size or dimension of the anatomical region of interest. The sphericity filtering method can further comprise determining or generating a gradient vector 35 at each point P2 of the set of points on the sphere 34. Each determined gradient vector 35 is indicative of a direction of a voxel value change and a magnitude of the voxel value change. Each determined gradient vector 35 may be determined or generated at each point P2 using a method or process configured to determine or generate a gradient at one or more subvoxel positions. A subvoxel position may be understood as a position between at least two voxels. For example, in some embodiments, each determined gradient vector 35 is generated at each point P2 based on a central difference approximation, which uses an interpolation function, such as a trilinear interpolation function. Volume data between at least two voxels may be interpolated using the interpolation function.

In other embodiments, each gradient vector is generated using a gradient reconstruction method, e.g. a direct gradient reconstruction method. For example, the gradient reconstruction method may use one or more partial derivatives of one or more quadratic or cubic interpolation polynomials, such as b-spline, Catmull-Rom spline or other spline function.

In some embodiments, the processing circuitry 22 is configured to detect a candidate anatomical region based a direction of each determined gradient vector 35 at each point P2 relative to the sphere 34. For example, a direction of each determined gradient vector 35 at each point P2 along the radius R of the sphere 34, e.g. towards or away from the centre P1 of the sphere 34, may be indicative of a candidate anatomical region comprising a spherical structure. In such embodiments, the determined gradient vectors 35 may be considered as being radially arranged on the sphere 34. One or more deviations of the determined gradient vector 35 from the direction along the radius R of the sphere 34 may be indicative of a decreased sphericity. In some embodiments, the sphericity filtering method comprises determining or generating an expected gradient vector 36 at each point P2.

In some embodiments, the processing circuitry 22 is configured to generate each expected gradient vector 36 such that each expected gradient vector 36 at each point P2 extends along a direction of the radius R, e.g. towards or away from the centre P1 of the sphere 34. In such embodiments, the expected gradient vectors 36 may be considered as being radially arranged on the sphere 34.

In other embodiments, the processing circuitry 22 is configured to generate each expected gradient vector 25 at each point P2 by determining a normalised vector based on a difference between a voxel value of the first sample 33*a* at the centre P1 and a voxel value at a point P2 and applying the normalised vector to a predefined sphere model.

FIG. 4B shows a schematic representation of a part of the generated sphere 34, including a plurality of expected gradient vectors 36. The sphericity filtering method can comprise determining an angle $\alpha$ between each expected gradient vector 36 and the determined gradient vector 35 at each point P2. Based on the determined angle $\alpha$ at each point P2 on the sphere 34, the processing circuitry 22 is configured to determine whether a first sample is a centre of a spherical structure. For example, an angle of approximately zero between each determined gradient vector 35 and each respective expected gradient vector 36 may indicate that the first sample on which the sphere 34 is centred is a centre of a spherical structure. One or more first samples that are part of or inside the sphere 34 may be considered as being part of the spherical structure. This in turn can be indicative of the candidate anatomical region. The angle $\alpha$ at each point P2 on the sphere may further be indicative of a variance of voxel value gradients on the sphere.

It will be appreciated that in other embodiments, the detection of the candidate anatomical region may be performed separately from the process shown in FIG. 2B.

In such other embodiment, the candidate anatomical region has been identified by segmentation. For example, the processing circuitry or the image processing circuitry may be configured to detect or identify the candidate anatomical region using a segmentation process or method.

In the present embodiment, at stage 32*c*, the processing circuitry 22 is configured to determine a second measure of the candidate anatomical region.

In examples where the candidate anatomical region comprises a gap or space, e.g. as described above in relation to the first measure, the second measure may comprise a dimension or size of the gap or space. In examples where the candidate anatomical region comprises a tubular structure, e.g. as described above in relation to the first measure, the second measure may comprise a vesselness, vessel branching or another measure. In examples where the candidate anatomical region comprises a spherical structure, e.g. as described above in relation to the first measure, the second measure may comprise a textural measure, such as a sphericity and/or variance, or another measure. It will be appreciated that the anatomical region of interest and the candidate anatomical region comprise the same type of anatomical region or structure. For example, both the anatomical region of interest and the candidate anatomical region may comprise a gap or space, a tubular structure, a spherical structure, as mentioned above, or another anatomical structure or region.

In examples where the candidate anatomical region comprises the gap or space described above, a distance L spanning the first samples, e.g. between at least two second samples, can be indicative of a size or dimension of the gap or space. The distance L is indicated in FIG. 3. For example, the processing circuitry 22 is configured to cast the plurality of lines from each first sample 33*a*, as described above, to determine the size or dimension of the gap or space.

In some embodiments, the processing circuitry 22 can be configured to determine the size or dimension of the gap or space based on the range of the first measure of the anatomical region of interest. This may include measuring a position of a nearest first sample above a lower bound of the range and a position of a nearest first sample below an upper bound of the range and determining a minimum distance between the first samples. The minimum distance corresponds to or represents a minimum size or dimension of the gap or space. However, it will be appreciated that in other embodiments, the processing circuitry 22 may be configured to determine an average size or dimension or a maximum size or dimension of the gap or space, e.g. based on all first samples in the gap or space. It will be appreciated that the processing circuitry is not limited to determining the size or dimension of the gap or space using the processes described herein. For example, in other embodiments, the processing circuitry may be configured to determine the size or dimension of the gap or space using another process or method.

In examples where the anatomical region of interest comprises a tubular structure, the processing circuitry 22 is configured to use the vesselness filtering method described above to determine a vesselness or vessel branching of the candidate anatomical region. For example, the processing circuitry 22 is configured to use the vesselness filtering method to determine how tubular the candidate anatomical region is.

In examples where the anatomical region of interest comprises a spherical structure, the processing circuitry 22 is configured to use the sphericity filtering method described above to determine a sphericity of the candidate anatomical region. For example, the processing circuitry 22 is configured to determine the sphericity of the candidate anatomical region based on the determined angle between each expected gradient vector 36 and each respective determined gradient vector 35 at each point P2.

It will be appreciated that in other embodiments, the determination of the second measure of the candidate anatomical region may be performed separately from the process shown in FIG. 2B. In such other embodiments, the processing circuitry may be configured to receive volume data comprising the candidate anatomical region. The volume data can further comprise a predetermined second measure of the candidate anatomical region. The volume data including the candidate anatomical region and the second measure of the candidate anatomical region have been obtained separately, e.g. from a previous medical scan. For example, the processing circuitry can be configured to receive the volume data from the data store. The volume data may also be referred to as scalar volume.

At stage 32*d*, the processing circuitry 22 is configured to determine whether the second measure is below the threshold, is within the range or corresponds, e.g. substantially corresponds, to the value of interest of the first measure.

At stage 32*e*, when the processing circuitry 22 determines that the second measure is below the threshold, is within the range or corresponds, e.g. substantially corresponds, to the value of interest of the first measure, the processing circuitry 22 determines that the first samples of the candidate anatomical region are part of the anatomical region of interest. For example, the processing circuitry 22 is configured to validate the candidate anatomical region as the anatomical region of interest.

Any of the process steps described above in relation to stages 30 to 36 shown in FIGS. 2A and 2B can be performed by the rendering circuitry 26.

In the process steps described above in relation to FIG. 2B, the processing circuitry 22 is configured to determine whether the one or more first samples are part of the anatomical region of interest based on the range, threshold or values of interest of the first measure. However, it will be appreciated that in other embodiments, the processing circuitry may be configured to determine whether the one or more first samples are part of the anatomical region of interest based on a segmentation mask of the anatomical region of interest or a part thereof. For example, the processing circuitry 22 may be configured to use a machine learning model, such as a deep learning model to generate the segmentation mask of at least the part or all of the anatomical region of interest. It will be appreciated that in other embodiments, the processing circuitry may receive the segmentation mask from the data store 16. The segmentation mask may be generated, for example by using the deep learning segmentation model as described in J. Wasserthal et al. (2023) "TotalSegmentator: Robust Segmentation of 104 Anatomic Structures in CT Images". In Radiology: Artificial Intelligence—arXiv: 2208.05868v2.

FIG. 5A illustrates a 2D image of an anatomical region of interest. The 2D image illustrated in FIG. 5A has been generated by projecting a MPR slab using the MIP algorithm. In the example shown in FIG. 5A, the anatomical region of interest includes a fracture 40*a* in a bone 40. In the image shown in FIG. 5A, an outline 42 of the bone is clearly visible. However, the fracture 40*a* is hardly visible, which can make the detection of the fracture 40*a* difficult.

FIG. 5B illustrates another 2D image of the anatomical region of interest. The 2D image illustrated in FIG. 5B has been generated by projecting a MPR slab using the MinIP algorithm. The image shown in FIG. 5B is based on the same MPR slab as the image shown in FIG. 5A. In the image shown in FIG. 5B, fracture 40*a* is clearly visible. However, the outline 42 of the bone is eroded.

FIG. 5C illustrates a 2D image of the anatomical region of interest that has been generated using the process described above in relation to FIGS. 2A and 2B. In this example, the first projection mode is different from the second projection mode. The first projection mode comprises the MinIP algorithm and the second projection mode comprises the MIP algorithm. For example, the first samples are part of the fracture 40*a* and have been projected using the MinIP algorithm. The second samples that are not part of the fracture 40*a* have been projected using the MIP algorithm. In other words, the projection mode for the first samples has been switched from the MIP algorithm to the MinIP algorithm. This leads to an improved image of the fracture 40*a* while preserving the outline 42 of the bone.

In other words, by projecting the first samples using the first projection mode and the second samples using the second projected mode, a detection and/or visualisation of the anatomical region of interest may be improved. In this example, the process described herein may allow for an improved visualisation of small or thin anatomical structures or regions, such as a thin fracture. For example, the process described herein may allow for the improved visualisation of an anatomical structure or region, such as a fracture or other anatomical structure or region, having a size smaller than 5 mm, such as a size between about 0.5 mm and about 2 mm. As such, in this embodiment, the threshold of the first measure may be about 5 mm and/or the range of the first measure may be between about 0.5 mm and about 2 mm. However, it will be appreciated that the threshold and/or range of the first measure is not limited to the exemplary values disclosed herein. The improved visualisation of small or thin anatomical structures or regions may allow for a quantitative measurement of the anatomical structures or regions with more accuracy. For example, the improved visualisation of small or thin anatomical structures or regions may allow for an extent and/or width of a fracture to be more accurately determined.

It can be seen from FIG. 5A that the gaps or spaces between different bones are also more clearly visible. An example of one of these gaps or spaces is indicated by reference numeral 40*b*. It should be understood that the process described above can be performed for a plurality of anatomical regions of interest that are part of or comprised in the slab. However, for sake of clarity the following description will only refer to the fracture 40*a*.

In the example shown in FIGS. 5A to 5C, the pixels associated with the fracture 40*a* have a lower intensity that the pixels associated with the bone 40. This is due to the voxel values associated with the fracture 40*a*, e.g. the fluid therein, (e.g. the first samples) being lower than the voxel value associated with the bone 40 (e.g. the second samples).

It will be appreciated that in other embodiments, one or more pixels associated with the anatomical region of interest may have an intensity that is higher than one or more pixels are located outside the anatomical region of interest. For example, the anatomical region of interest may comprise an abnormality of a lung of a patient or other subject. The abnormality may be in the form of a pocket filled with a fluid, such as air. In such embodiments, one or more voxel values associated with the anatomical region of interest, e.g. the first samples, are higher than one or more voxel values associated with one or more second samples that are not part of the anatomical region of interest. The pixels with the higher intensity may be visible in the image as bright features or structures, which may also be referred to as bridges.

FIG. 6A illustrates a 2D image of the anatomical region of interest that has been generated by projecting a MPR slab using the AveIP algorithm. In the example shown in FIG. 6A, the anatomical region of interest also includes the fracture 40*a* described above. In this example, the fracture 40*a* is visible. However, it is difficult to determine an extent and/or width of the fracture 40*a* and the outline 42 is eroded.

FIG. 6B illustrates another 2D image of the anatomical region of interest that has been generated using the process described above in relation to FIGS. 2A and 2B. In the example shown in FIG. 6B, the anatomical region of interest also includes the fracture 40*a* described above. In this example, the first projection mode is different from the second projection mode. The first projection mode comprises the MinIP algorithm and the second projection mode comprises the MIP algorithm. For example, the first samples that are part of the fracture 40*a* have been projected using the MinIP algorithm and the second samples that are not part of the fracture 40*a* have been projected using the MIP algorithm.

In the example shown in FIG. 6B, size or dimension of the fracture 40*a* was more accurately determined compared to the fracture 40*a* shown in FIGS. 5A to 5C. For example, the threshold and/or range of the first measure used in the process to project the image shown in FIG. 6B may be different, e.g. larger, compared to the threshold and/or range of the first measure used in the process to project the image shown in FIG. 5C. As such, a larger number of first samples was projected using the first projection mode compared to the example described above in relation to FIG. 5C. Compared to the 2D image shown in FIG. 6A, a width of the fracture 40*a* may be more accurately determined from the 2D image shown in FIG. 6B. In addition, a definition of the outline 42 is improved in the 2D image shown in FIG. 6B.

FIG. 7 illustrates a 2D image of a mask 44 that is defined by pixels associated with the anatomical region of interest. For example, the processing circuitry 22 may be configured to generate one or more first indicators. The first indicators may be indicative of one or more pixels that are associated with the first samples that have been projected using the first projection mode. The processing circuitry 22 may be configured to generate one or more second indicators. The second indicators may be indicative of one or more pixels that are associated with the second samples that have been projected using the second projection mode. The processing circuitry 22 may be configured to generate a mask based on the first and/or second indicators. The mask 44 may be used in a masking process of another image or for overlaying on another image.

In the example shown in FIG. 7, the processing circuitry 44 has generated the mask based on the first indicators. As such, the mask 44 is defined only by the pixels that have been projected using the first projection mode, which in this example comprises the MinIP algorithm. The mask 44 may be presented to a user in the form of a colour tint to an intensity of the pixels associated with the first and/or second samples.

FIG. 8 illustrates a 2D image of the anatomical region of interest that has been generated using the process described above in relation to FIGS. 2A and 2B. The anatomical region of interest also includes the fracture 40*a* described above. In this example, the first projection mode is the same as the second projection mode. The first and second projection modes comprise the AveIP algorithm. The processing circuitry 22 is configured to project the first samples associated with the fracture 40*a* separately from second samples that are not part of the fracture 40*a*.

In order to generate the 2D image shown in FIG. 6A, the voxel data values of all samples of the MPR slab were averaged. In contrast, in the example shown in FIG. 8, the voxel values of the first samples that are part of the fracture 40*a* were averaged and the voxel values of the second samples were averaged separately. As such, the processing circuitry 22 can change what samples are used to project an image of the fracture 40*a*.

FIG. 9 illustrates a 2D image of another anatomical region of interest that has been generated by projecting a MPR slab using the MIP algorithm. The 2D image shown in FIG. 9 shows a lung 46 of a patient or other subject. In this embodiment, the region of interest includes abnormalities 48 in the lung 46, which in this embodiment are due to lung emphysema. The abnormalities 48 may have a sponge-like appearance. In this embodiment, the measure of the anatomical region of interest comprises a textural measure. The textural measure may be based on or comprise a sphericity and/or variance.

FIG. 10 illustrates a 2D image of the anatomical region of interest shown in FIG. 9 that has been generated using the process described above in relation to FIGS. 2A and 2B. In this embodiment, the processing circuitry 22 is configured to define a value of interest of the first measure, which in this embodiment is a sphericity value of interest. In this embodiment, the sphericity value of interest is a maximum sphericity value of the abnormalities 48. The processing circuitry 22 is configured to detect the abnormalities 48 using the sphericity filtering method described above. The processing circuitry 22 is configured to determine a sphericity for each of the abnormalities 48 using the sphericity filtering method described above. The determined sphericity is considered to be the second measure. The processing circuitry 22 is configured to determine whether the determined sphericity of each of the abnormalities corresponds, e.g. substantially corresponds, to the sphericity value of interest. When the determined sphericity value of one or more abnormalities corresponds, e.g. substantially corresponds, to the sphericity value of interest, the processing circuitry 22 is configured to determine that one or more first samples associated with these abnormalities 48 are part of the anatomical region of interest.

As mentioned above, the processing circuitry 22 is configured to project the first samples associated with these abnormalities 48 using the first projection mode. The processing circuitry 22 is configured to project one or more second samples that are not part of the region of interest using the second projection mode. In this embodiment, the first projection mode comprises the MIP algorithm and the second projection mode also comprises the MIP algorithm. As discussed above, in relation to FIG. 8, the processing circuitry 22 is configured to project the one or more first samples separately from the one or more second samples, when the first and second projection modes are the same.

Based on the sphericity value of interest, the processing circuitry 22 is configured to adjust a window width and/or window level to single out the abnormalities 48 in the 2D image shown in FIG. 10. The abnormalities 48 in the 2D image shown in FIG. 10 include a plurality of spherical shapes. The region comprising the abnormalities in FIG. 10 may also be referred to as a grainy region. From the 2D image shown in FIG. 10, it may be possible to determine a number of spherical shapes, which in turn may allow for a quantitative measure of the abnormalities 48.

It will be appreciated that any of the above features may also apply to embodiments where the anatomical region of interest comprises a tubular structure.

Certain embodiments provide medical visualization method comprising a slab consisting of a number of samples determined by a camera/transform, a metric to detect if a sample is part of a gap, determining the length of an identified gap, two opposing intensity modes, such as MaxIP and MinIP, operating on the slab sample, in which each sample is determined as a potential gap candidate, for gap candidates the length of the gap is identified and the gap is validated if the length is within user set bounds and if there are any valid gap sample the intensity mode is switched from the default (MaxIP) to the gap mode (MinIP) and non gap samples are discarded.

Bridges (high intensity analogue to a gap) may be detected and the mode may be switched between different intensity modes.

The detection may be done inline while rendering the image by casting lines in different directions from a sample and measuring the length of the gap in that direction.

The detection of the gap may have been done as a segmented object and the rendering pass may only perform the distance measure.

The detection of the gap and the minimum length of the gap at each voxel may have been determined beforehand and may be passed in as a separate scalar volume.

All the samples may be used for the gap detected intensity projection.

The switched pixels may be written into a mask for use as an overlay or further processing.

Both intensity modes may be the same, for example AvIP, and only the rejection of non gap/bridge samples may differ.

A gap threshold may be defined relative to the W/L settings for the view.

The gap detection may be changed to another local geometric measurement, such as vesselness or vessel branching, texture metrics using sphericity and variance and image analysis based segmentation mask coverage replacing intensity based gap as the highlighting region.

Whilst particular circuitries have been described herein, in alternative embodiments functionality of one or more of these circuitries can be provided by a single processing resource or other component, or functionality provided by a single circuitry can be provided by two or more processing resources or other components in combination. Reference to a single circuitry encompasses multiple components providing the functionality of that circuitry, whether or not such components are remote from one another, and reference to multiple circuitries encompasses a single component providing the functionality of those circuitries.

Whilst certain embodiments have been described, these embodiments have been presented by way of example only, and are not intended to limit the scope of the invention. Indeed the novel methods and systems described herein may be embodied in a variety of other forms; furthermore, various omissions, substitutions and changes in the form of the methods and systems described herein may be made without departing from the spirit of the invention. The accompanying claims and their equivalents are intended to cover such forms and modifications as would fall within the scope of the invention.

The invention claimed is:

1. A medical image processing apparatus comprising processing circuitry configured to:

receive a slab comprising a plurality of samples determined by a camera model;

determine whether one or more first samples of the plurality of samples are part of an anatomical region of interest; and project the slab along a view direction onto an image plane to form an image, wherein the processing circuitry is configured to define at least one of:

a threshold of a first measure of the anatomical region of interest:

a range of the first measure of the anatomical region of interest; or a value of interest of the first measure of the anatomical region of interest, the processing circuitry is configured to at least one of:

determine a second measure of a candidate anatomical region, the candidate anatomical region comprising the one or more first samples, or receive a predetermined second measure of the candidate anatomical region; and determine whether the second measure is below the threshold of the first measure, is within the range of the first measure or corresponds to the value of interest of the first measure, and in response to a determination that the one or more first samples are part of the anatomical region of interest, the processing circuitry is configured to:

project the one or more first samples using a first projection mode; and project one or more second samples of the plurality of samples that are not part of the anatomical region of interest using a second projection mode, one or more first pixels of the image being associated with the one or more first samples and one or more second pixels of the image being associated with the one or more second samples.

2. The apparatus according to claim 1, wherein the first and second projection modes are the same or different.

3. The apparatus according to claim 1, wherein the first projection mode comprises at least one of a minimum intensity projection (MinIP) algorithm, a maximum intensity projection (MIP) algorithm and an average intensity projection (AveIP) algorithm and the second projection mode comprises at least one of a minimum intensity projection (MinIP) algorithm, a maximum intensity projection (MIP) algorithm and an average intensity projection (AveIP) algorithm.

4. The apparatus according to claim 2, wherein when the first and second projection modes are different at least one of the first and second projection modes comprises a minimum intensity projection (MinIP) algorithm and at least one other of the first and second projection modes comprises a maximum intensity projection (MIP) algorithm.

5. The apparatus according to claim 2, wherein when the first and second projections modes are the same, the processing circuitry is further configured to project the one or more first samples separately from the one or more second samples.

6. The apparatus according to claim 2, wherein when the first and second projections modes are the same, the first and second projection modes each comprise an average intensity projection (AveIP) algorithm.

7. The apparatus according to claim 1, wherein;

a voxel value associated with the one or more first samples is higher than a voxel value associated with the one or more second samples; or the voxel value associated with the one or more first samples is lower than the voxel value associated with the one or more second samples.

8. The apparatus according to claim 1, wherein the threshold, the range or the value of interest of the first measure is defined based on a selected window width and/or window level to be applied to the image.

9. The apparatus according to claim 1, wherein the first measure of the anatomical region of interest comprises at least one of:

a dimension or size of the anatomical region of interest;

a vesselness of the anatomical region of interest or vessel branching of the anatomical region of interest; and a textural measure.

10. The apparatus according to claim 1, wherein the processing circuitry is further configured to determine that the one or more first samples of the candidate anatomical region are part of the anatomical region of interest, when the second measure of the candidate anatomical region is below the threshold of the first measure, is within the range of the first measure or corresponds to the value of interest of the first measure.

11. The apparatus according to claim 1, wherein the processing circuitry is further configured to detect the candidate anatomical region.

12. The apparatus according to claim 11, wherein the processing circuitry is further configured to detect the candidate anatomical region by casting a plurality of lines from at least one of the one or more first samples in a plurality of directions and to determine the second measure of the candidate anatomical region.

13. The apparatus according to claim 1, wherein the processing circuitry is further configured to determine whether the one or more first samples of the plurality of samples are part of the anatomical region of interest based on a segmentation mask of at least a part of the anatomical region of interest.

14. The apparatus according to claim 1, wherein the candidate anatomical region has been identified by segmentation.

15. The apparatus according to claim 1, wherein the processing circuitry is further configured to receive volume data comprising the candidate anatomical region, the volume data including the predetermined second measure of the candidate anatomical region.

16. The apparatus according to claim 1, wherein one or more pixels of the image are associated with the one or more first samples and wherein the one or more pixels define a mask for use in a masking process of another image or for overlaying on another image.

17. The apparatus according to claim 1, wherein the anatomical region of interest comprises a space or gap and the first measure comprises a size or dimension of the space or gap.

18. A medical image processing method comprising:

receiving a slab comprising a plurality of samples determined by a camera model;

determining whether one or more first samples of the plurality of samples are part of an anatomical region of interest; and projecting the slab along a view direction onto an image plane to form an image, wherein the method comprises defining at least one of:

a threshold of a first measure of the anatomical region of interest;

a range of the first measure of the anatomical region of interest; or a value of interest of the first measure of the anatomical region of interest, the method comprises at least one of:

determining a second measure of a candidate anatomical region, the candidate anatomical region comprising the one or more first samples, or receive a predetermined second measure of the candidate anatomical region; and determining whether the second measure is below the threshold of the first measure, is within the range of the first measure or corresponds to the value of interest of the first measure, and in response to a determination that the one or more first samples are part of the anatomical region of interest, the method comprises:

projecting the one or more first samples using a first projection mode; and projecting one or more second samples of the plurality of samples that are not part of the anatomical region of interest using a second projection mode, one or more first pixels of the image being associated with the one or more first samples and one or more second pixels of the image being associated with the one or more second samples.

19. A medical image processing apparatus comprising processing circuitry configured to:

receive a slab comprising a plurality of samples determined by a camera model;

determine whether one or more first samples of the plurality of samples are part of an anatomical region of interest; and project the slab along a view direction onto an image plane to form an image, wherein the processing circuitry is configured to define at least one of:

a threshold of a first measure of the anatomical region of interest;

a range of the first measure of the anatomical region of interest; or a value of interest of the first measure of the anatomical region of interest, the processing circuitry is configured to at least one of:

determine a second measure of a candidate anatomical region, the candidate anatomical region comprising the one or more first samples, or receive a predetermined second measure of the candidate anatomical region; and determine whether the second measure is below the threshold of the first measure, is within the range of the first measure or corresponds to the value of interest of the first measure, and in response to a determination that the one or more first samples are part of the anatomical region of interest, the processing circuitry is configured to:

project the one or more first samples using a first projection mode; and project one or more second samples of the plurality of samples that are not part of the anatomical region of interest using a second projection mode.

* * * * *